(12) United States Patent
Sandstrom

(10) Patent No.: US 7,808,648 B2
(45) Date of Patent: Oct. 5, 2010

(54) METHOD AND DEVICE FOR OPTICAL DETERMINATION OF PHYSICAL PROPERTIES OF FEATURES, NOT MUCH LARGER THAN THE OPTICAL WAVELENGTH USED, ON A TEST SAMPLE

(75) Inventor: Torbjorn Sandstrom, Pixbo (SE)

(73) Assignee: Micronic Laser Systems AB, Taby (SE)

( * ) Notice: Subject to any disclaimer, the term of this patent is extended or adjusted under 35 U.S.C. 154(b) by 193 days.

(21) Appl. No.: 11/742,414

(22) Filed: Apr. 30, 2007

(65) Prior Publication Data

US 2007/0252986 A1 Nov. 1, 2007

Related U.S. Application Data

(60) Provisional application No. 60/796,179, filed on Apr. 28, 2006.

(51) Int. Cl.
G01B 9/02 (2006.01)
G01B 11/02 (2006.01)

(52) U.S. Cl. ........................ 356/495; 356/511
(58) Field of Classification Search ................. 356/495, 356/511–516
See application file for complete search history.

(56) References Cited

U.S. PATENT DOCUMENTS

| | | | |
|---|---|---|---|
| 3,829,219 A | 8/1974 | Wyant | |
| 4,639,139 A | 1/1987 | Wyant et al. | |
| 4,832,489 A | 5/1989 | Wyant et al. | |
| 5,661,560 A * | 8/1997 | Ozaki | 356/364 |
| 5,777,740 A * | 7/1998 | Lacey et al. | 356/495 |
| 5,898,181 A | 4/1999 | Vurens | |
| 5,936,734 A | 8/1999 | Johs et al. | |
| 6,134,011 A | 10/2000 | Klein et al. | |

(Continued)

FOREIGN PATENT DOCUMENTS

EP 1324137 7/2003

(Continued)

OTHER PUBLICATIONS

Azzam, Division of amplitude photopolariimeter(DOAP) for the simultaneous measurement of all four Stokes parameters of light, Journal of Modern Optics, vol. 29, No. 5, May 1982, pp. 685-689.*

(Continued)

*Primary Examiner*—Michael A Lyons
(74) *Attorney, Agent, or Firm*—Haynes Beffel & Wolfeld LLP; Ernest J. Beffel, Jr.

(57) ABSTRACT

A method and device for optical determination of physical properties of features, not much larger than the optical wavelength used, on a test sample are described. A beam is split into reference and illuminating beams having known polarization. The test sample is exposed to the illuminating beam and recombined to form an image. The image is detected using at least one sensor, which may be cameras. A point-to-point map of polarization, phase and power is extracted from data representing the image. Optionally, the sensor may be a camera. The sensor may detect at least three optical parameters, such as a Stokes vector, a Jones vector, a Jones matrix, a Mueller matrix or a coherency matrix.

32 Claims, 9 Drawing Sheets

U.S. PATENT DOCUMENTS

| | | |
|---|---|---|
| 6,251,564 B1 | 6/2001 | Lin et al. |
| 6,307,627 B1 | 10/2001 | Vurens |
| 6,515,745 B2 | 2/2003 | Vurens et al. |
| 6,989,896 B2 | 1/2006 | Wen et al. |
| 7,009,691 B2 * | 3/2006 | VanWiggeren et al. ..... 356/73.1 |
| 7,061,621 B2 * | 6/2006 | Krause ....................... 356/491 |
| 7,428,057 B2 * | 9/2008 | De Lega et al. ............. 356/511 |
| 2003/0095264 A1 | 5/2003 | Ruchet |
| 2004/0161675 A1 | 8/2004 | Lin |
| 2005/0046855 A1 * | 3/2005 | Davidson .................... 356/451 |
| 2005/0046865 A1 | 3/2005 | Brock et al. |

FOREIGN PATENT DOCUMENTS

| | | |
|---|---|---|
| WO | WO 00/39601 | 7/2000 |
| WO | WO-03079111 | 9/2003 |

OTHER PUBLICATIONS

International Search Report Application No. PCT/EP2007/003751 mailed Jul. 6, 2007.

Amary P et al.: "A new sensor for trench depth monitoring: the TDM 200", Proceedings of the SPIE, SPIE, Bellingham, VA, US, vol. 5343, No. 1, 2003, pp. 244-254.

Bashara N et al., "Ellipsometry and Polarized LIght", Elsevier, 1987.

Huard S, "Polarization of Light", John Wiley & Sons, 1997.

International Search Report for International Application No. PCT/SE2004/001700 mailed on May 2, 2005.

"An example of the use of point diffraction interferometry," HH Chuaqui et al 1984 J. Phys. E: Sci. Instrum. 17, 268-270; doi: 10.1088/0022-3735/17/4/003.

* cited by examiner

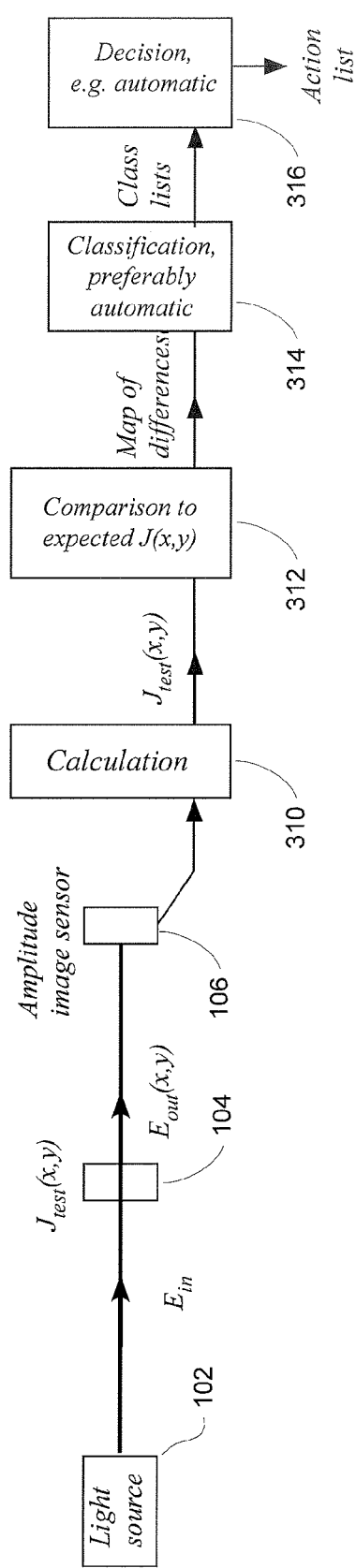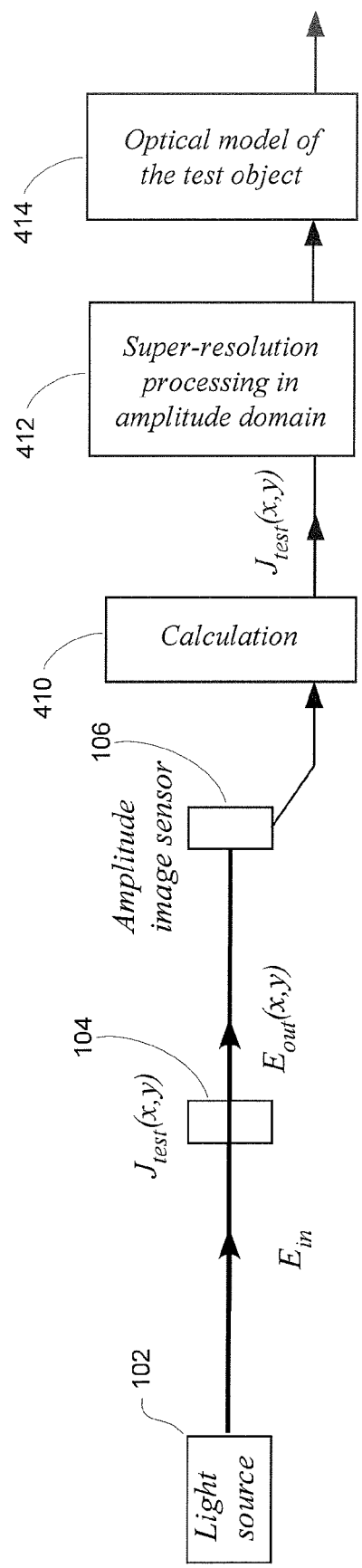
Fig. 3
Fig. 4

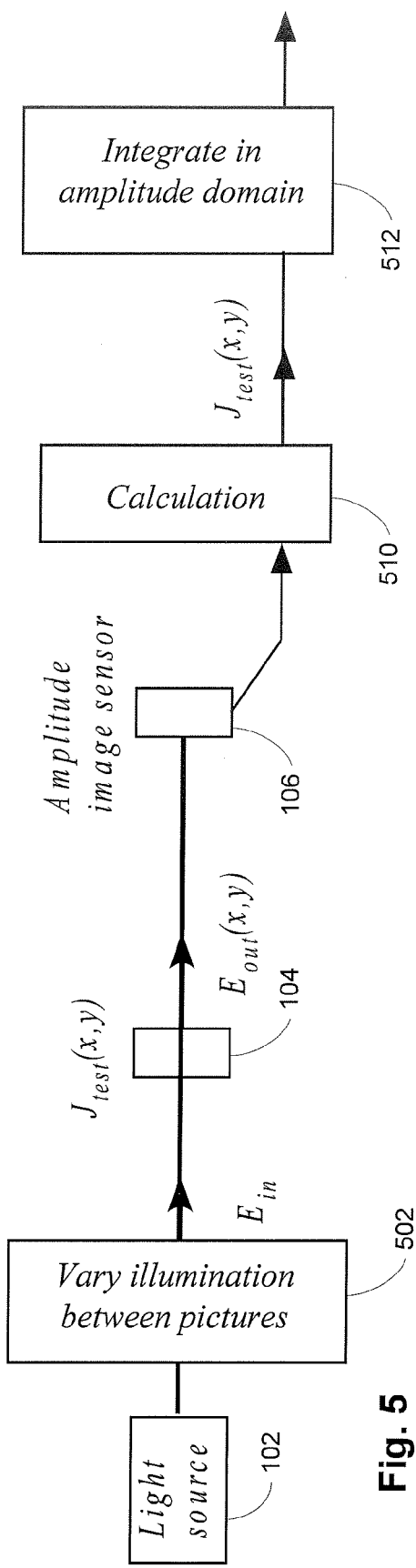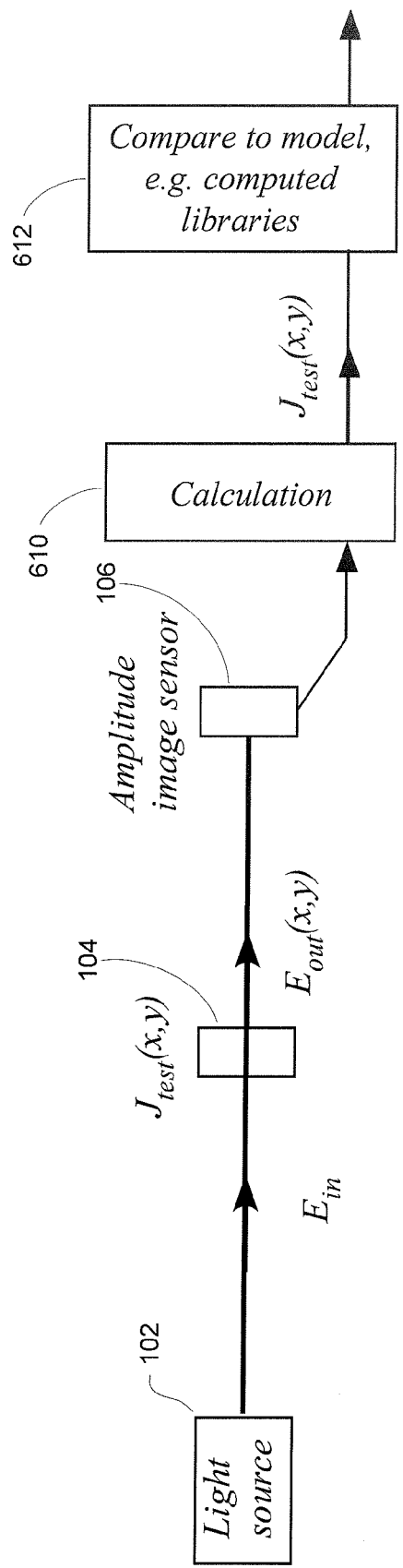
Fig. 5
Fig. 6

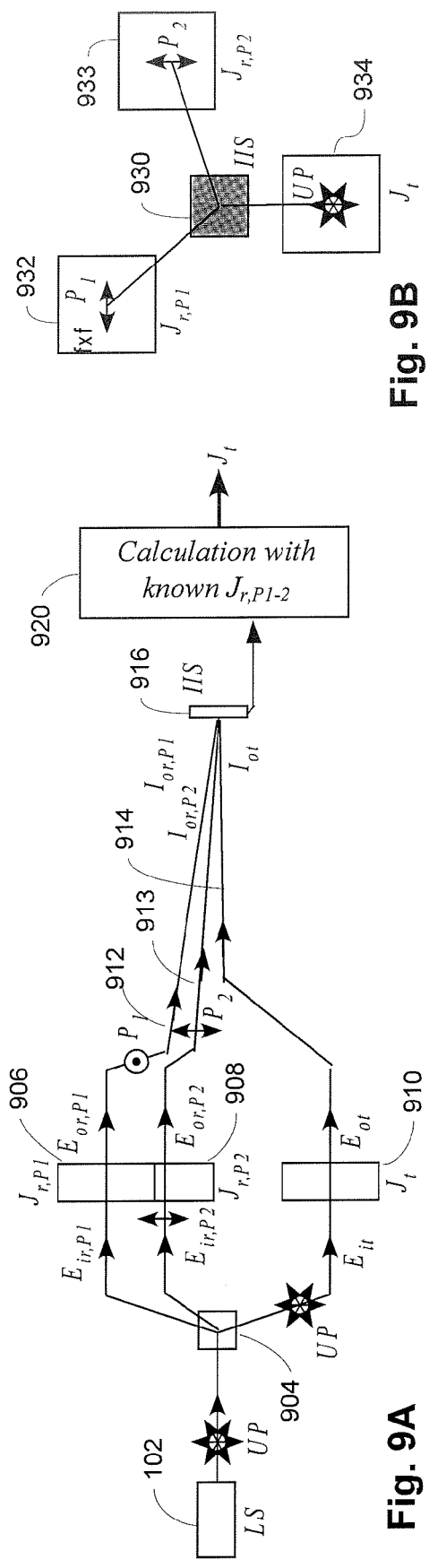
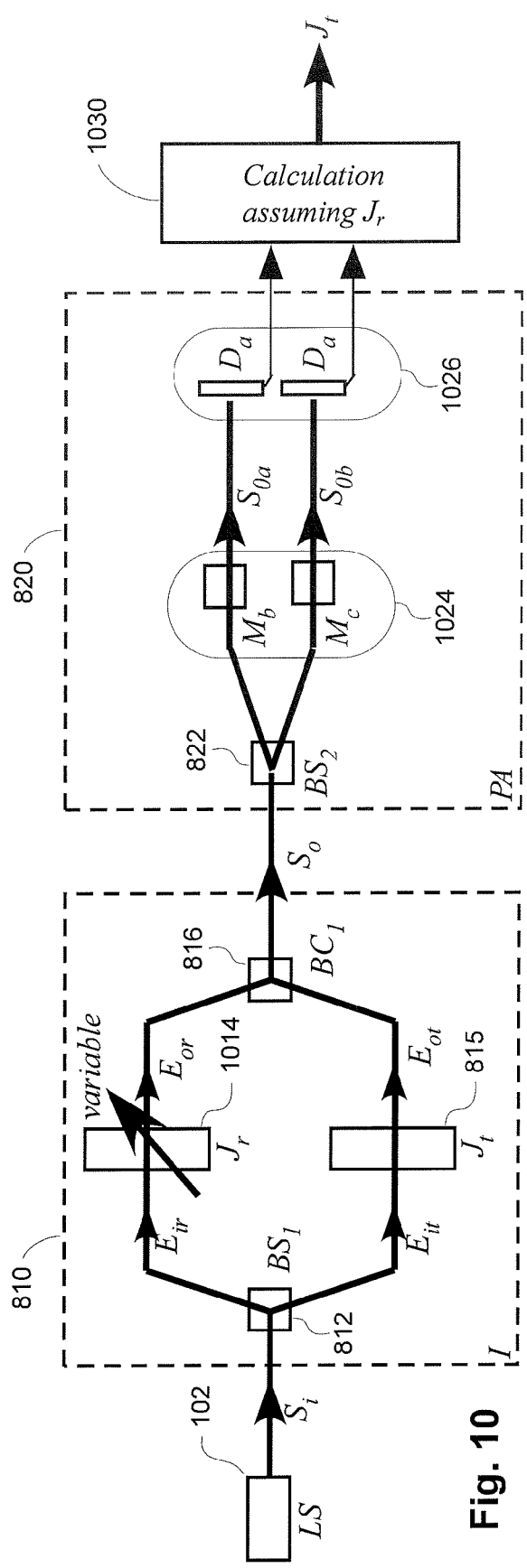

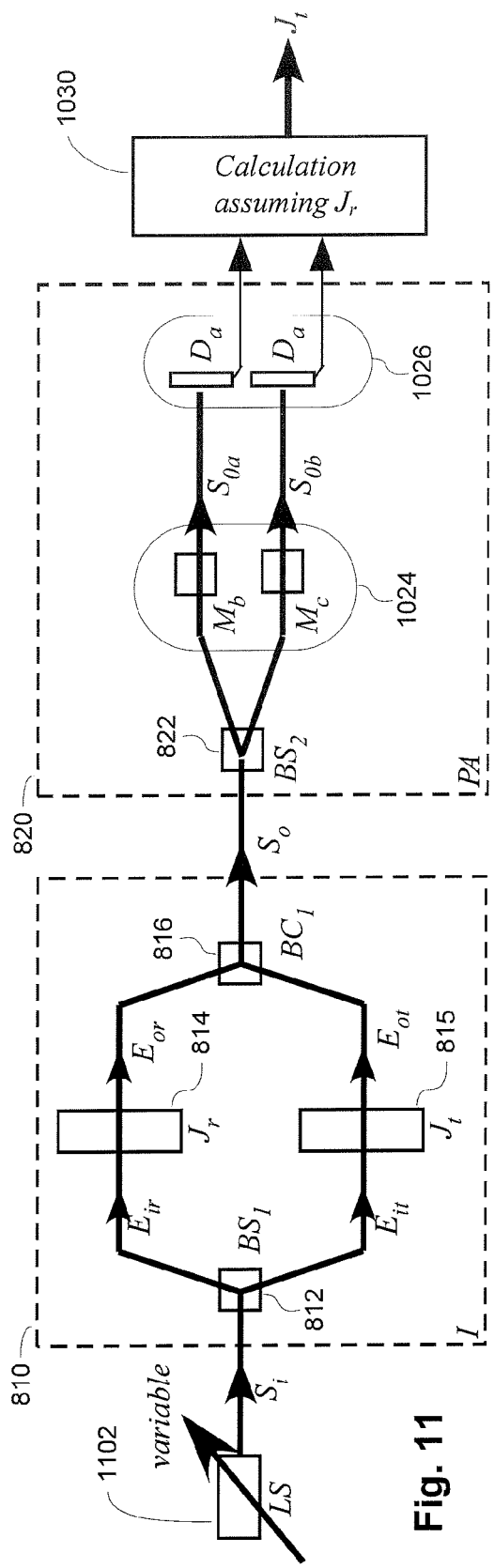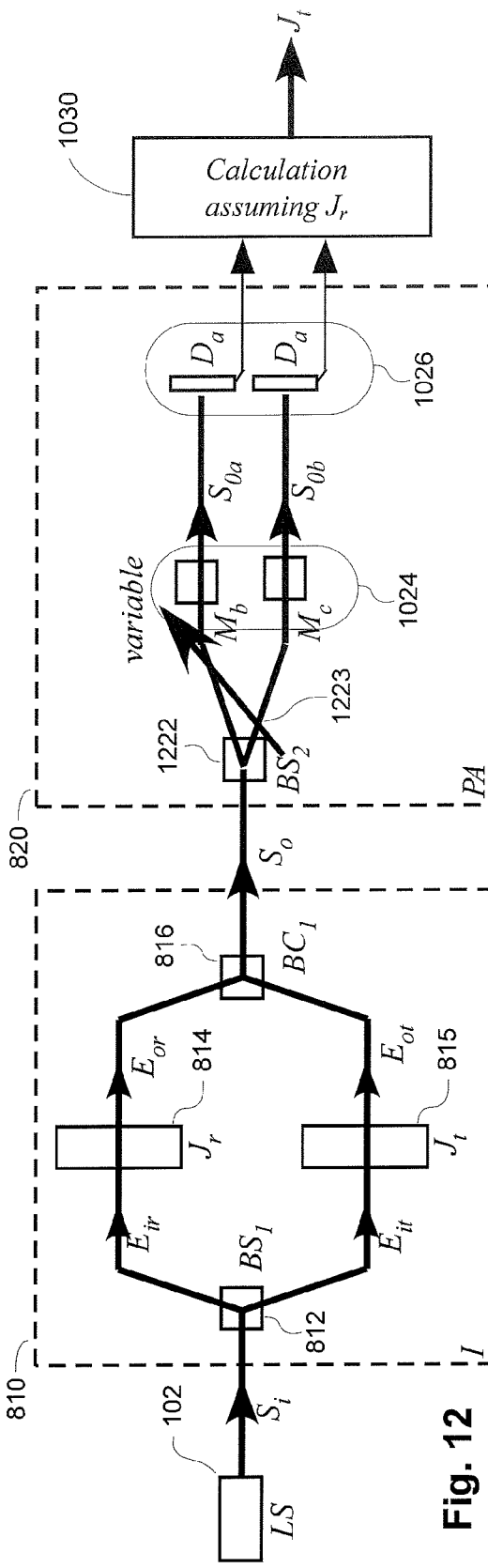

METHOD AND DEVICE FOR OPTICAL DETERMINATION OF PHYSICAL PROPERTIES OF FEATURES, NOT MUCH LARGER THAN THE OPTICAL WAVELENGTH USED, ON A TEST SAMPLE

RELATED APPLICATION

This application claims priority to and the benefit of U.S. Provisional Application No. 60/796,179, filed 28 Apr. 2006, with a title substantially the same as this application, and naming as inventor (for U.S. purposes) Torbjorn Sandstrom. The provisional application is hereby incorporated by reference.

BACKGROUND OF THE INVENTION

This application discloses a new method to record an image. It relates to microscopy and surface analysis in many scientific and technical fields. In particular it relates to the imaging and inspection of surfaces used in microelectronics: non-patterned and patterned wafers and photomasks. In the sense that it records electric amplitude, it relates to holography. Applications include microscopy, defect inspection, scatterometry, and optical metrology.

This work improves on interferometry, e.g. white-light interferometry, where successive interferograms with a phase-shift between them are used to construct an image which contains both phase and magnitude of the surface reflection coefficients (ref: patent by James Wyant). It also improves on ellipsometry where the relative magnitudes and phases between two states of polarization are measured, and the surface properties of a sample are deduced from an optical model of the surface (ref: patent by HDI, book by Azzam and BAshara). Finally it improves on direct-to-digital holography where the absolute phase and amplitude of light reflected or transmitted over an area is recorded in a single image. It also improves on scatterometry where the variation of reflection by polarization, angle of incidence, and/or wavelength is used to fit geometrical parameters in a model of microstructures, thus determining their size or shape.

In normal optical imaging, the intensity of the light is recorded. This intensity is the square of the magnitude of the electric field or amplitude:

$$I(x,y)=|E(x,y)|^2 \quad (1)$$

However, the electric field also has a phase that is lost in the detector. In the general case, it also has two polarizations P1 and P2 (or, sometimes labelled p and s,) which are typically linearly polarized with E-fields parallel to the x and y axises respectively, when xyz is an orthogonal coordinate system and z is the local direction of propagation. Thus, when only intensity is recorded, we have very little knowledge about the actual electric field in the image. We only know that:

$$|E_{p1}(x,y)|^2+|E_{p2}(x,y)|^2=I(x,y) \quad (2)$$

Images are often recorded in order to be used for analysis of the optical properties of a surface. Because only intensity information is recorded, the power of analysis is limited. This is the subject of so-called inverse imaging problems, where one or several images are combined with a priori knowledge to analyze surface characteristics beyond what the image alone shows. Generally, many objects can be inversely reconstructed from an intensity image, since they give the same intensity image, and one object must be chosen as more likely than another based on statistical properties or a priori knowledge. This has been the way most imaging and photography has worked since the dawn of photography and microscopy. If, however, more of the phase and amplitude information could be recorded in the image plane, a fuller analysis would be possible.

In a so-called phase-stepping interferometer, multiple interferograms are recorded with a known phase shift in the reference beam between the images. The set of images are used to calculate the variation in optical phase, i.e. the variation in optical path length, leading to a height map of a surface. In white-light interferometry (one variety of phase-stepping interferometry) a broad wavelength range is used in the interferometer, and the condition for exactly equal path length in test and reference beam can be established, thereby resolving the problem with multiple solutions in the interferometer. The white-light interferometer looks like a normal microscope with a camera. After analysis, the computer serving the white-light interferometer outputs one image similar to a normal microscope image and another image which is the optical phase or the height of the surface. The latter has a resolution of single-digit nanometers or better. In essence, phase-stepping and white-light interferometers record the magnitude and phase of the electric field from a series of images. The phase-stepping and white-light interferometers are good for accurate height metrology.

Another way to capture more information is by ellipsometry. In ellipsometiy a light beam is reflected onto the surface, normally at a high angle of incidence. The incident beam is polarized in a known way, typically having linear polarization with the polarization direction at 45 degrees to the plane of incidence. The surface affects light polarized parallel ("p") and perpendicular ("s") to the plane of incidence differently. One can imagine that at the point of reflection the beam is split into a p and an s beam. They are reflected with different attenuation and phase delay and recombined instantly to give a polarization that is different from the incident polarization. By measuring the polarization before and after and comparing the two, the difference in amplitude and phase between the p and s beams can be determined. By comparison to an optical model of the surface, two selected parameters of the surface (often thickness and refractive index of a surface film) can be determined. Ellipsometry can also produce images by the combination of the polarizing system with imaging optics. Because it uses the difference between two components of the same light beam as the information-carrying quantity, ellipsometry has low noise and is extremely sensitive to small surface changes.

A third background technology is so-called direct-to-digital holography, or DDH. The image from a microscope is superposed on the image detector by a reference blanket illumination beam, coherent with the light from the image. The reference beam has an angular offset from the light from the image and a dense fringe pattern is produced on the sensor. The contrast of the fringes gives the magnitude of the E-field in the image, and the fringe placement gives the phase. Thus an image with both magnitude and phase can be calculated as in the phase-stepping interferometer, but from a single recorded image. DDH has the benefit that it is fast. With a single exposure needed at each geometric position, DDH is suitable for scanning large surfaces for defects. The defects found may not be visible in a normal microscope image. DDH can therefore be used as a complement to bright- and dark-field images for defect inspection, especially for defects that extend in the z direction.

All these three background techniques extract information about the E-field reflected or transmitted by the sample; however they extract just part of the full information. Ellipsometry sees only the difference between the polarizations; phase-stepping and DDH see only an average phase and magnitude of the two polarizations.

An opportunity arises to collect more information at once, in a single instrument. Better and more complete optical analysis components and systems may result.

BRIEF DESCRIPTION OF THE DRAWINGS

FIG. 3 shows a system based on FIG. 1 for finding anomalies on a sample.

FIG. 4 shows a system for recording a super resolved image of a surface or other 2D object.

FIG. 5 shows a system for synthetic aperture imaging where several amplitude images with different illumination directions are recorded and added in the amplitude domain.

FIG. 6 shows a system for determination of shape and other parameters of features on a test sample by fitting the measured data phase and polarization data to an electromagnetic or optical model of the features.

FIGS. 9A-9B show a development of the so called direct-to-digital holographic image method which simultaneously records amplitude images for two polarizations FIGS. 10-12 shows a method to determine the Jones matrix by means of multiple recorded exposures.

DETAILED DESCRIPTION

Figure 1:
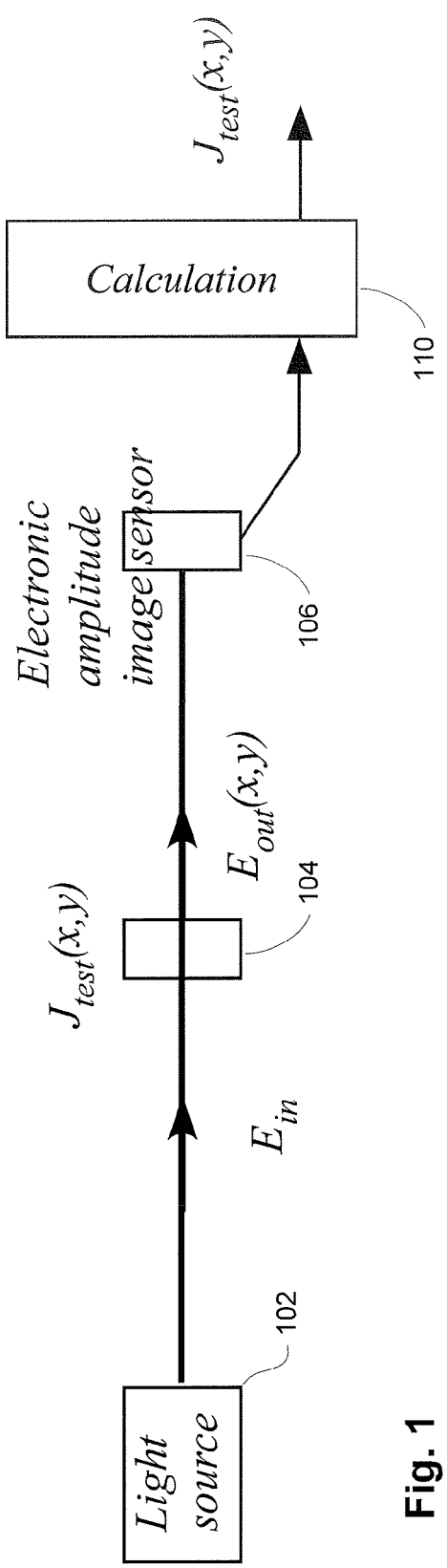
FIG. 1 shows a system for measuring the polarization and phase properties of a test sample.

The following detailed description is made with reference to the figures. Preferred embodiments are described to illustrate the present invention, not to limit its scope, which is defined by the claims. Those of ordinary skill in the art will recognize a variety of equivalent variations on the description that follows.

We have brought the imaging science one step further by inventing a method and apparatus, together with several embodiments, to analyze surfaces and other objects by recording both phase and magnitude of two polarizations. We believe that such an imaging technique will have great utility, especially for surfaces with structures small compared to the wavelength of the light, e.g. wafers with microelectronic devices, microoptical devices, nano-size structures and photomasks.

When the phase and magnitude for both polarization states can be recorded through focus, the third (near-field) E-component can be calculated. The light could be numerically back-propagated through the optics and the properties of the object could be determined in great detail. This would make inverse problems much simpler and would increase the surface-analyzing power of optical instruments significantly. We believe that other benefits include more efficient processing of amplitude and phase images for increased resolution, and that synthetic aperture methods can be used to compute images with resolution beyond the limits of the numerical aperture of the actual imaging lens.

We disclose s a new type of camera that records not the intensity, but the full complex E-field amplitude of the light. Holograms are known to record amplitude, but only imperfectly: they do not record the direction of the E-vector, i.e. the polarization, and they do not separate between positive and negative field directions. The technology disclosed records a fully or partially coherent, fully or partially polarized image with intensity, polarization, and phase at each point; or, expressed differently, the point-by-point amplitude and phase for two polarization states.

Images are nearly always recorded with the purpose of learning about the properties of an object or test sample. In normal intensity images much of the information, namely the phase and the direction of the E-field, are lost and the analysis of the sample is limited. A vast literature exists on how to learn more about an object from its image; Keywords are "inverse scattering", inverse imaging", "super-resolution", "model-based analysis", and "scatterometry". There is a vast difference in the analysing power in optics and in radar technology, since in radar the field E is recorded while in optics one normally only knows the square of the modulus of the field $|E|^2$.

We believe that with the methods described in this application the methods of radar analysis, e.g. aperture synthesis, can be used in optics. Furthermore, all inverse problems, which are all about recovering lost information, are easier to solve if more of the information was not lost in the first place. Many important technical applications exist for inverse problems: defect inspection for patterned and non-patterned wafers, photomasks, flat-panel devices, and analysis of structure near and below the wavelength of the light in microelectronics, biology, and material science.

Representations of Light

For this disclosure, it is necessary to use polarization terminology. Below follows a brief introduction to the relevant qualities and their relations. Many textbooks exist where polarization is described. We have tried to follow the terminology of Serge Huard, Polarization of Light, Wiley, New York 1997.

A quasimonochromatic fully polarized beam can be represented by a complex column vector called the Jones vector:

$$E = \begin{bmatrix} E_x \\ E_y \end{bmatrix}$$

For partially polarized light this can be generalised to a Jones field matrix with two columns, each one of them being a normal Jones vector and each column representing the length in two orthogonal "pure" states of polarization:

$$E = E_1 + E_2 = \begin{bmatrix} E_{1x} 0 \\ E_{2y} 0 \end{bmatrix} + \begin{bmatrix} 0 E_{2x} \\ 0 E_{2y} \end{bmatrix} = \begin{bmatrix} E_{1x} & E_{2x} \\ E_{2y} & E_{2y} \end{bmatrix}$$

The effect on the beam by a component, e.g. a polarizer, retarder, rotation, or just a time delay, is represented by a multiplication by a complex Jones matrix (different from the Jones field matrix):

$$E_o = J E_i$$

$$J = \begin{bmatrix} J_{1x} & J_{2x} \\ J_{2y} & J_{2y} \end{bmatrix}$$

An alternative representation is the real 4×1 column Stokes vector which is based on intensity when the beam is analysed with respect to different polarization planes. In contrast to the Jones vector or field matrix, the Stokes vector does not give the phase of the light.

$$S = \begin{bmatrix} P_0 \\ P_1 \\ P_2 \\ P_3 \end{bmatrix}$$

The effect of a component is represented by a multiplication with a real 4×4 Mueller matrix M $S_0 = MS_i$ A third representation is the coherence Matrix theta defined as time averages between the field components. The coherence matrix relates in a simple way to the Stokes vector:

$$\Theta = \begin{bmatrix} \Theta_{xx} & \Theta_{xy} \\ \Theta_{yx} & \Theta_{yy} \end{bmatrix}$$

$$= \begin{bmatrix} \langle E_x E_x^* \rangle & \langle E_x E_y^* \rangle \\ \langle E_y E_x^* \rangle & \langle E_y E_y^* \rangle \end{bmatrix}$$

$$= \frac{1}{2} \begin{bmatrix} P_0 + P_1 & P_2 - iP_3 \\ iP_3 - P_2 & P_0 - P_1 \end{bmatrix}$$

The effect of a component on the coherence matrix is represented by the following equation where J is the Jones matrix:

$$\Gamma_o = J \Gamma_i J^*$$

In this way the different representations (and a few more) can be converted into each other. For this purpose we have found the Jones field matrix is most suitable, since like the Stokes vector and the coherence matrix it represents partially polarized beams, but also retains the phase of the beam, which is lost in the Stokes and coherence matrix formalisms.

The fact that there is no established representation of a polarized or partially polarized beam fits well with the fact that there is no instrument which quantifies the polarization including the phase and the power. For the phase to be relevant, a phase reference is needed. In an image, this can be the average phase of the image, or the phase at a point where it is known. It is only in differential measurements where the absolute phase has importance; However in an image it can be seen as a differential measurement.

Embodiments 1-8

Figure 8:
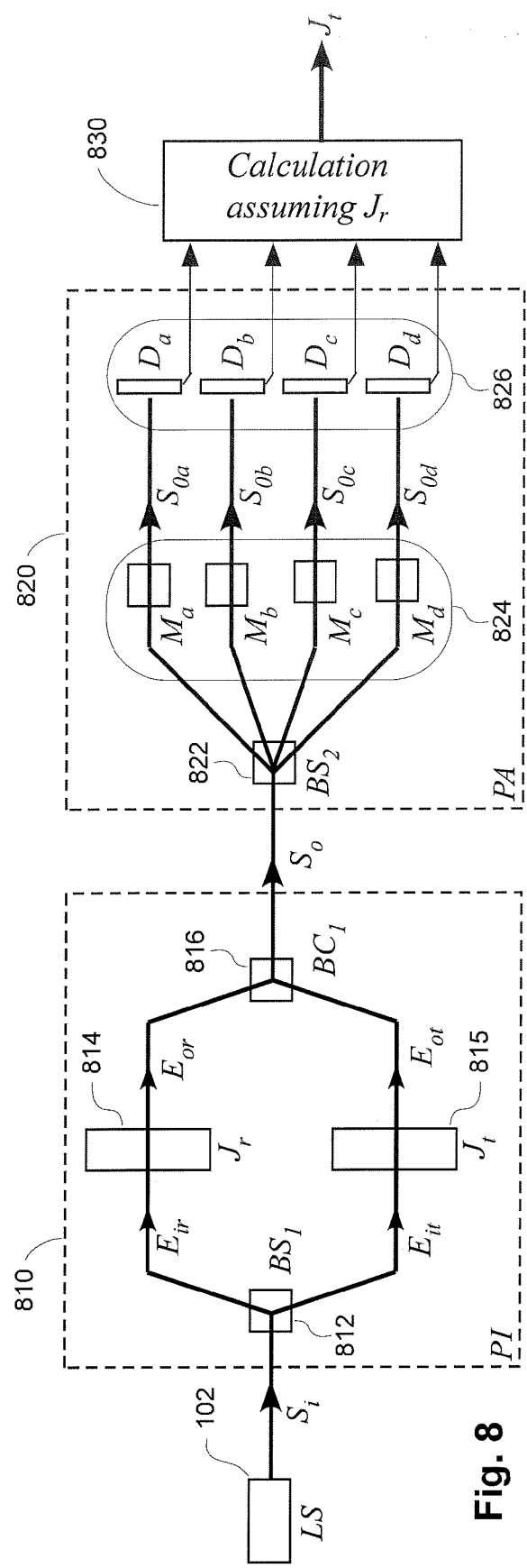
FIG. 8 shows a method for recording an amplitude including power, polarization and phase in the image.

FIG. 1 shows a system for measuring the polarization and phase properties of a test sample, and how they vary across the surface, e.g. the Jones matrix for every location on a surface with a common phase and amplitude reference. The system uses an electronic amplitude image sensor (106) to record the power, polarization and phase at each point. The light source (102) may be any light source, typically not fully polarized. It may be a pulse source, such as an excimer or solid state laser, or a continuous one. Some light sources may have high coherence and others less coherence. The test sample (104) is illuminated by the light source. It typically is a surface, either in reflected or transmitted mode. Two varieties of electronic amplitude image sensors are depicted in FIGS. 8-9. The calculation module (110) takes as input the data collected in one or more samplings from the image sensor. It outputs a bit map with polarization, power and phase data at the pixels. A Jones matrix is a useful example of representing attributes of the electric field.

Figure 2:
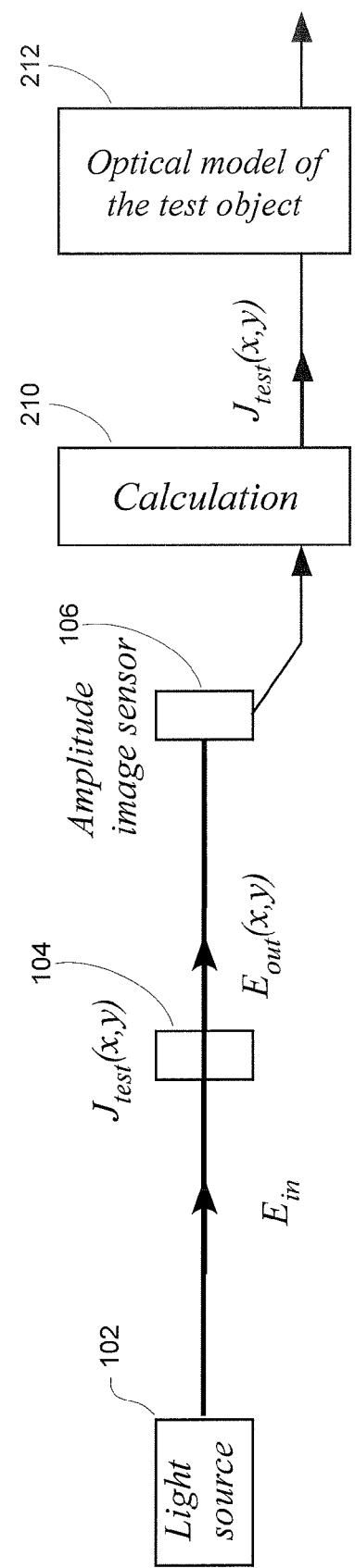
FIG. 2 shows a system for determining maps of optical or physical parameters over a sample.

FIG. 2 shows a system for determining maps of optical or physical parameters over a sample, e.g. a surface, by using the system in FIG. 1 and an optical model of the surface which relates such properties to the polarization and phase properties of reflected or transmitted light. The relationship can be explicit or implicit and it can consist of a look-up table or library. The optical model (212) of the test object is a map of the test object in terms of height, layer thickness, topography, width/density/placement/shape of microstructures, birefringence, composition, surface quality, defects, etc. It is a physical representation of what the surface must be, given the polarization map of the surface.

FIG. 3 shows a system based on FIG. 1 for finding anomalies on a sample, where the measured polarization and phase map are compared to an expected value or map and the differences are classified into one or several types of anomalies, e.g. defects in a wafer or photomask pattern. In one stage (312), we are looking for defects by comparing the expected to the actual. A map of differences is classified (314). Lists of classified defects are subjected to decision making (316).

FIG. 4 shows a system for recording a super resolved image of a surface or other 2D object. Super resolution is a class of image processing that discerns characteristics of the object which cannot be clearly seen. An amplitude image including phase information is recorded and a super resolving filter is applied (412) to the amplitude image, e.g. by inverse convolution by a super resolving function or by fitting of a parametric model of the sample using a priori knowledge like the knowledge that the object is a pattern in chrome. It produces a map of the test object with improved resolution (414).

Figure 17:
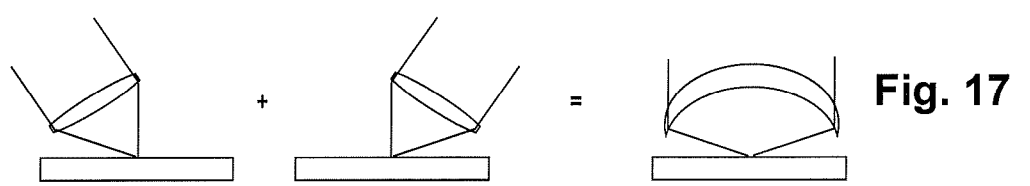
FIG. 17 conceptually shows the merging of two images into one with higher resolution.

FIG. 5 shows a system for synthetic aperture imaging where several amplitude images with different illumination directions are recorded and added in the amplitude domain (512), forming a combined amplitude image that corresponds to the image from a larger aperture. In radar, this is called a synthetic aperture. This embodiment produces an image with resolution better than the physical aperture limitations. The construction of a synthetic aperture from images taken at differing angles is depicted in FIG. 17.

FIG. 6 shows a system for determination of shape and other parameters of features on a test sample (612) by fitting the measured phase and polarization data to an electromagnetic or optical model of the features, e.g. by searching iteratively for a match between the output data of an electromagnetic model as a function of the desired parameters, or by comparing the data to a library computed beforehand of the same output data versus the studied parameters. More explanation is given in the flowchart, FIG. 16.

Figure 7:
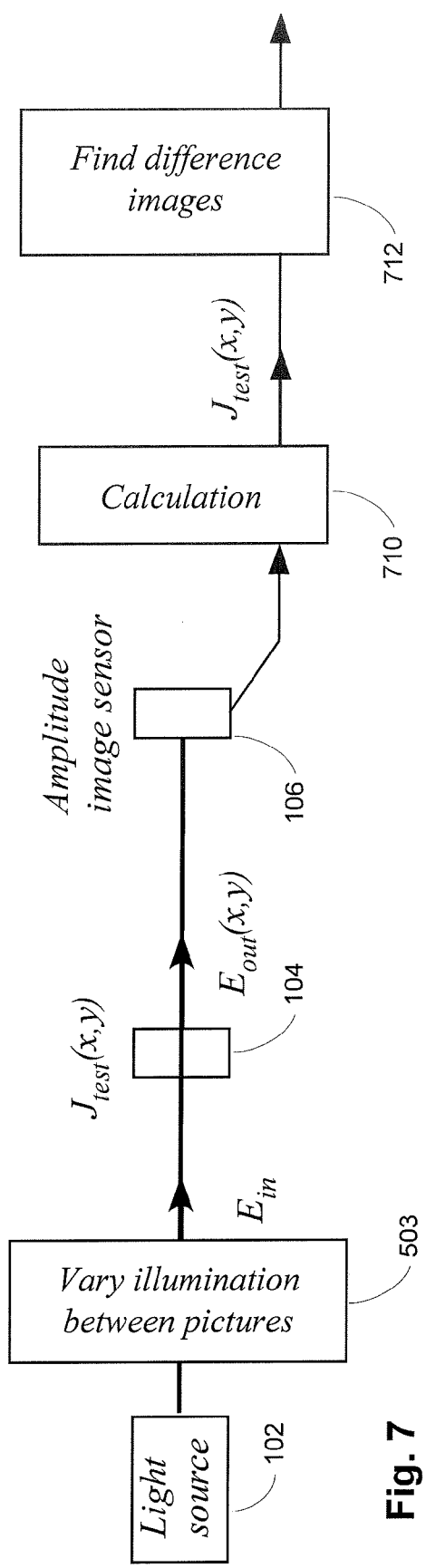
FIG. 7 is a more powerful system for determination of shape and other parameters of a test sample.

FIG. 7 is a more powerful system for determination of shape and other parameters of a test sample using the method described in relation to FIG. 6 and with additional information (712) coming from the recording of multiple amplitude and phase images with varying illumination, angle of incidence or angular spread at the sample, coherence, polarization or polarization variation over the illumination input range, wavelength or wavelength range or a combination of any of the other parameters.

FIG. 8 shows a method for recording amplitude including power, polarization and phase in the image. A light source (102), preferably not fully polarized, is split by a beam splitter (812) and processed against a reference surface (814), such as a simple mirror, and test surface (815). The beams are recombined by a beam combiner (816). A second beam splitter (822). A series of polarization filters Ma-Md (824) process legs of the split beam. After filtering, the split beams are detected (826).

The method can be combined with imaging so that an image is produced that represents the power, polarization, and phase at the exit plane of the object for each point. There are several equivalent representations: Jones matrix or Mueller matrix plus phase for the sample; Jones vector, Stokes vector with phase, or coherence matrix with phase; or power, polarization and phase for the light leaving the sample. These can be converted into each other as described in Serge Huard: Polarization of light and other textbooks. However, in treatments of polarization it is customary to leave out the phase and sometimes the power in the description of a light beam. These are measured here and used in the analysis of the sample.

Alternatively, the polarization filters (824) could be arranged over adjacent pixels, as in a RGB detector array, so that only one detector array would be required. The detector array can be super sampled so that multiple pixels fit into a single resolved portion of the image.

An incoming beam is split in an interferometer by a polarizing beam splitter, and one of the beams incurs amplitude and phase changes from the test sample. The Jones matrix Jt, Jr represents the action of the optics in the reference beam.

The beams are recombined and analysed by a Stokes-vector analyser, here a division of amplitude analyser using four photodetectors Da to Dd and a polarization splitting network represented by the beam splitter BS2 and the Mueller matrices of the polarization filters Ma to Md. Explanations for the division of amplitude Stokes vector analyser can be found in a publication by R. M. A. Azzam "Division of amplitude polarimeter" (approx 1980). The input beam is preferably not fully polarized, and since the Stokes vector analysed by the polarization analyses PA is not fully polarized, it has four free parameters from which can be determined the Jones vector of the light produced by the sample.

If the scheme in FIG. 8 is combined with an imaging system and the four detectors are image sensors, e.g. CCD cameras, the method will produce an image of the sample where each point has a known Jones vector with both phase and power are known. The Jones vector can be used to calculate point-by-point Jones matrices of the sample. Two elements can be derived directly. The other two need additional measurements with different input polarizations or beam splitter settings.

FIG. 9A shows a development of the so called direct-to-digital holographic (DDH) image method which simultaneously records amplitude images for two polarizations, thereby recording a Jones vector in each image point. Compared to the normal DDH method, a second reference channel (906, 908) is added with a different angle of incidence on the image sensor so that a second set of fringes is produced. Each reference beam (912, 913) produces fringes only with its own polarization state in the image of the sample and if the two reference beams have complementary polarizations, e.g. x and y linear or left- and right-handed circular, the full Jones vector will be recoded. There will be an unknown absolute phase difference between the two polarizations, due to the different paths, which has to be determined independently, e.g. by looking at a sample or an area of a sample that is known to have no difference between the polarization states.

FIG. 9A shows a setup implementing the method and 9B the same setup seen from the image intensity image sensor. The test surface (910) produces a test beam (914). An image sensor (916) samples the beams. A result is calculated (920). The Jones matrices in the reference beams represent the delay and attenuation of the optical system while Jt is the Jones matrix of the sample. FIG. 9B indicates that the three beams are displaced or tilted in both x and y directions from the central path.

More reference beams can be added for bringing out more information or more redundancy from each recording. The condition is that they do not interfere with each other, e.g. if the have different wavelength or in a pulsed system different times of arriving on the sensor. The image sensor in FIG. 9A is oversampled since fine fringes need to be resolved in resolved in every resolved part of the object. The phase and amplitude is calculated by processing the pixel-to-pixel differences in illumination on the sensor.

FIGS. 10-12 show a method to determine the Jones matrix by means of multiple recorded exposures, as opposed to FIGS. 8, 9A and 9B which do the recoding in a single recording. The method uses an interferometer, I, and a polarization analyser, PA. Between the recordings one parameter is varied, and the figures show a number of embodiments.

FIG. 10 varies the reference beam in the interferometer, e.g. phase stepping. A simple variation in the reference surface (1014) varies the distance. Alternatively, a polarizing surface could be rotated. By varying the reference beam, the number of polarizing filters (1024) and detectors (1026) can be decreased.

FIG. 11 varies a property of the illuminating light source (1102), e.g. the wavelength or the polarization. By making two or more measurements or recordings with different settings of the illuminator or image system more information can be extracted from the surface by inverse methods. The power of discrimination increases and the risk of false solutions is reduced.

FIG. 12 varies the analysed states in the polarization analyser (820). For example, a photoelastic modulator available from the company Hinds can be excited with ultrasound to vary its polarization. (This approach can also be applied to FIG. 10 or 11, as well.) The variable component can be placed before or after the beam splitter or it could be incorporated into the filters 1024.

Figure 13:
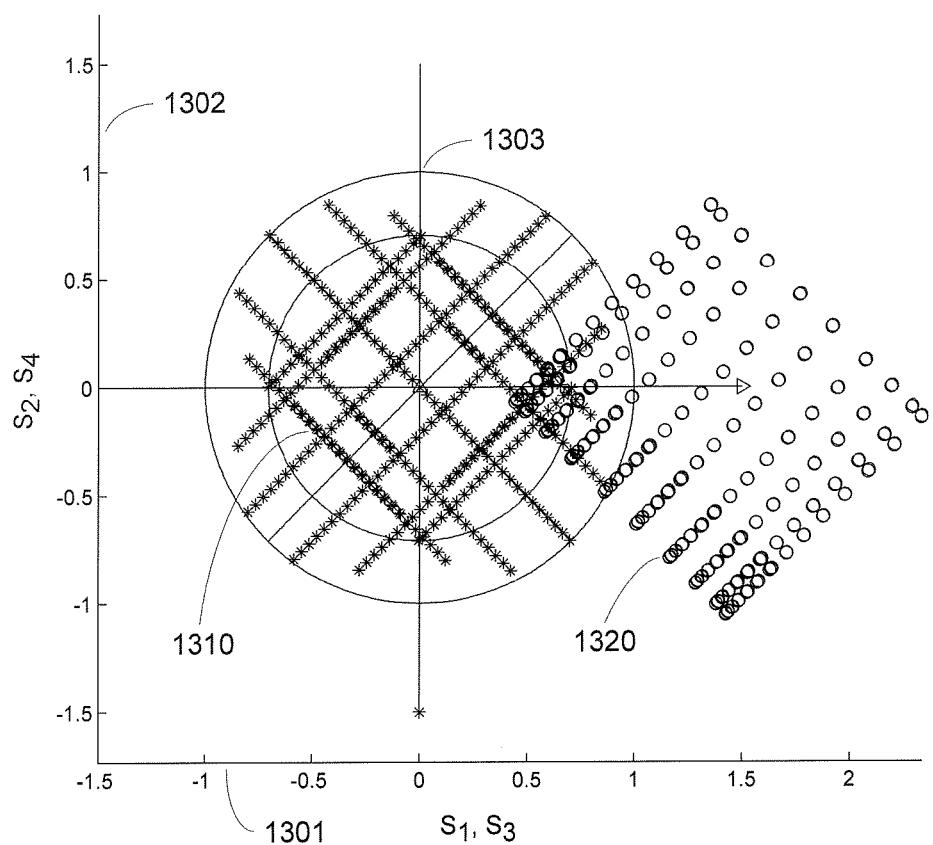
FIG. 13 shows the measured components (simulated) of the detected Stokes vector in one example embodiment when both diagonal elements of the Jones matrix of the sample surface changes magnitude and phase.

FIG. 13 shows the measured (simulated) components of the detected Stokes vector in one example embodiment (FIG. 8) when both diagonal elements of the Jones matrix of the sample surface changes magnitude and phase. The x-axis (1301) represents the s1 element of the Stokes vector. The y-axis (1302) is the second s2 element. The cross and bulls eye (1303) plot s3 and s4. Round markers (1320) are for S1 and S2 and stars (1310) for S3 and S4. By using all four parameters, one can unambiguously determine the diagonal elements.

Figure 14:
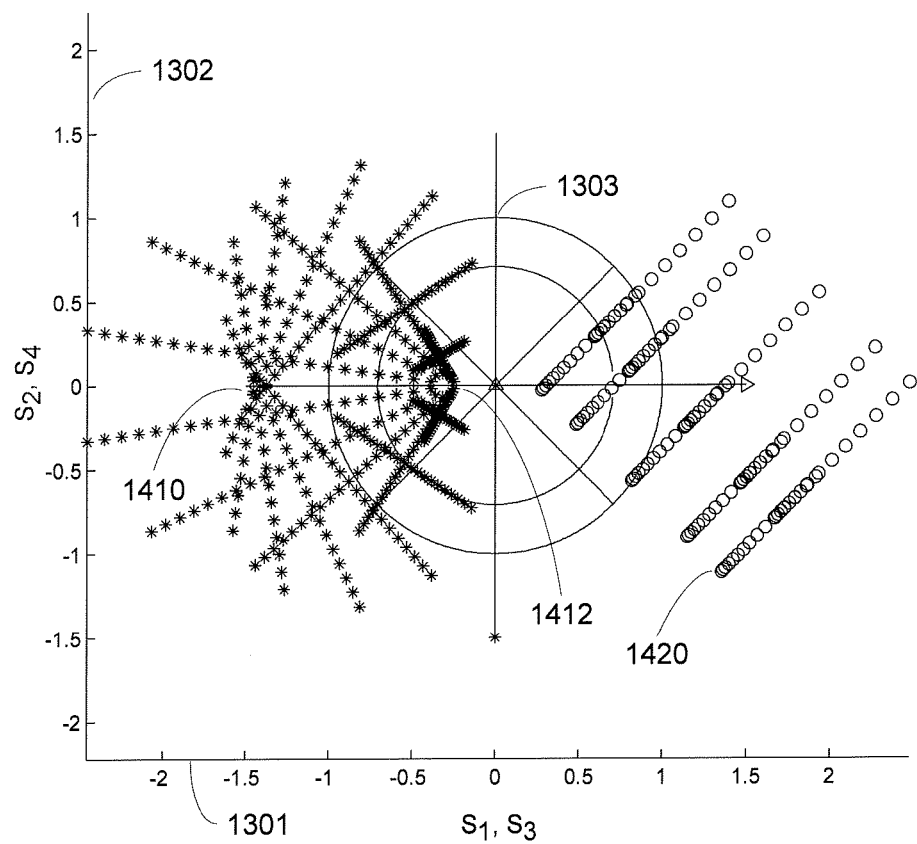
FIG. 14 shows the measured components (simulated) of the detected Stokes vector in another example embodiment (different beam splitter) when both diagonal elements of the Jones matrix changes magnitude and phase.

FIG. 14 shows the measured (simulated) components of the detected Stokes vector in another example embodiment (different beam splitter) when both diagonal elements of the Jones matrix changes magnitude and phase. Round markers are for S1 and S2 and stars for S3 and S4.

Figure 15:
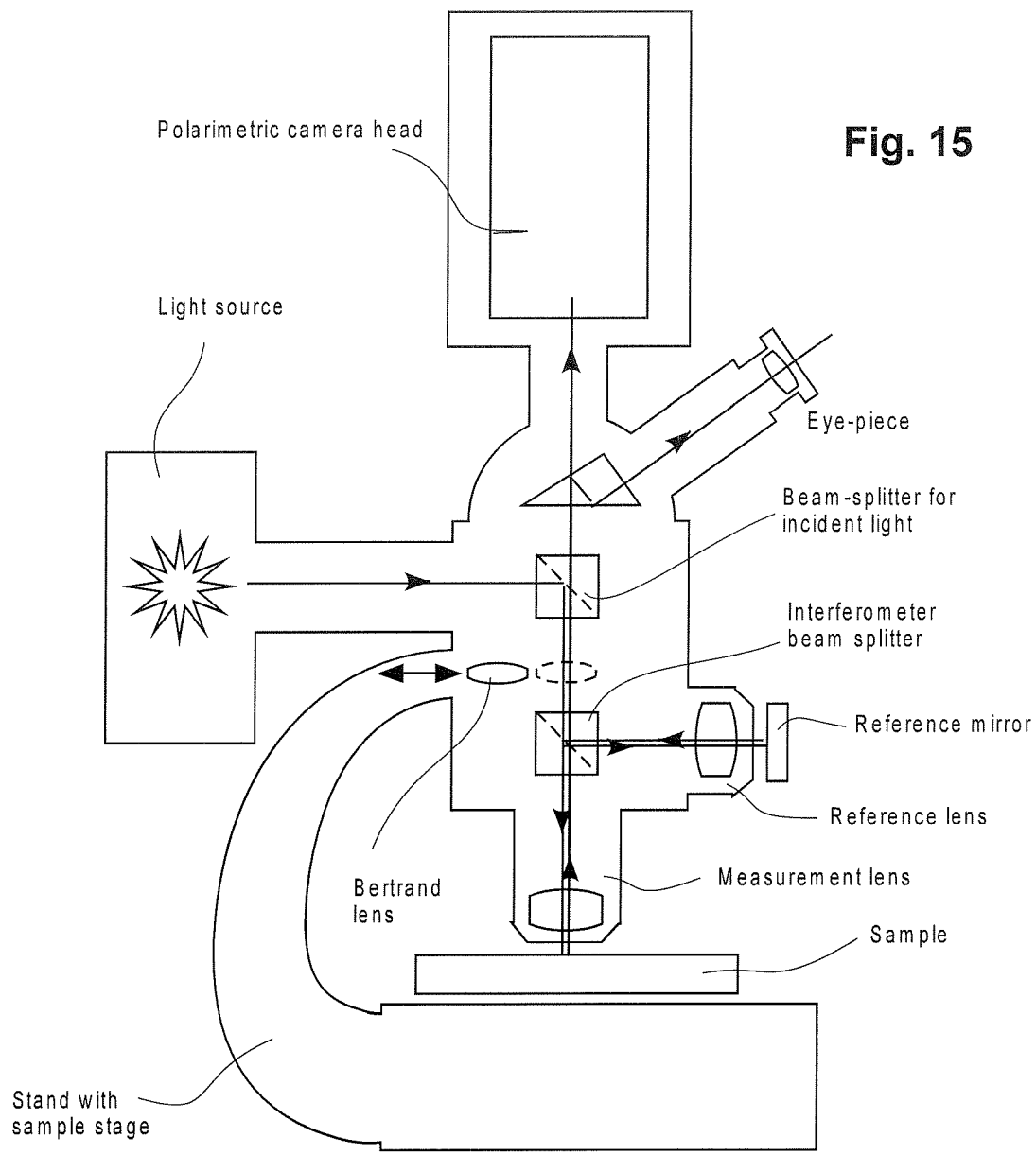
FIG. 15 depicts an optical microscope for incident illumination.

FIG. 15 depicts an optical microscope for incident illumination. The microscope is built with a Link interferometer and a reference mirror in the reference leg. The light source is partially polarized or non-polarized and the beam splitters are weakly polarizing. Thus both the light reflected from the sample and the reference surface are partially polarized and interfere as partially polarized beams as will be described below. The detector may be a polarimetric camera as described in FIG. 8 or 9. The image is recorded, processed and stored on a digital computer. The image is stored as a bitmap with the phase and amplitude for two directions of the electric field in every pixel. Therefore the image can be numerically propagated forward and backward, i.e. the focus of the image can be changed after it has been recorded. The image can be transmitted, e.g. by email, and the receiving person can scan focus through the surface and compare the local electric field to that simulated be an electromagnetic model. The full Jones matrix may also be computed in every pixel from two or more measurements. The analysis may be uniform in every pixel, or a fraction of the pixels may have the phase and amplitude or Jones matrix information. The full analysis can be done in a small subset of pixels numbering 1, 2, 4, 16, 64, 256, or more.

Alternatively, such as for the study of periodic structures, the Fourier transform of the image can be recorded with phase and magnitude for two polarizations. Or the image can be recorded with the full Jones matrix in every pixel. A Bertrand lens is included for this purpose. The image with full electric field amplitude may be recorded and transformed numerically to the aperture plane or it can be recorded in the aperture plane by means of the Bertrand lens and transformed numerically to the image or object plane.

Figure 16:
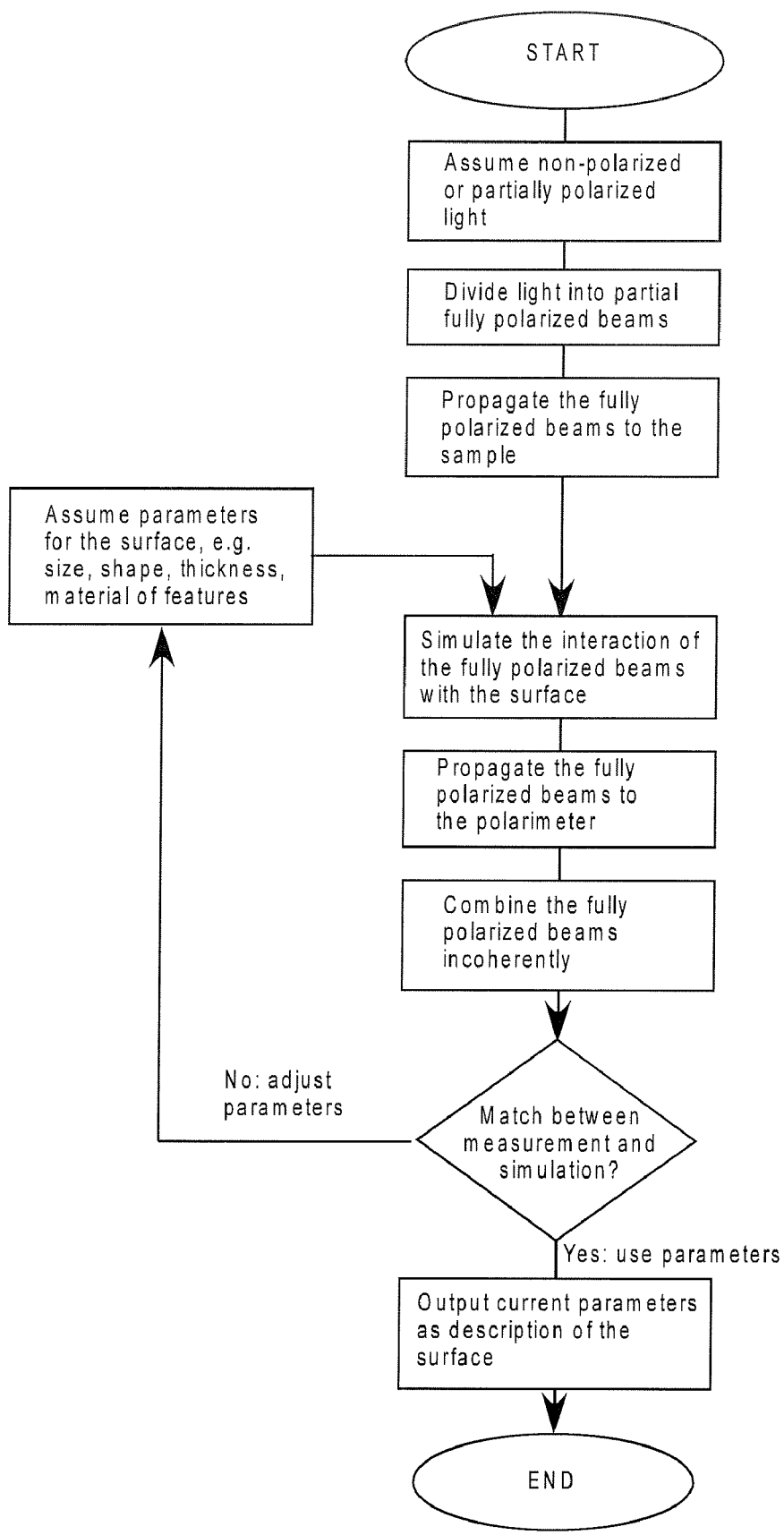
FIG. 16 shows a procedure for inverse determination of surface parameters.

FIG. 16 shows a procedure for inverse determination of surface parameters.

Modeling the Partially Polarized Interferometer

The following is an example how the calculation of the partial coherence interference can be done. The incoming beam is characterized by a Stokes vector $S_{in}$. The beam can be described as a superposition of two beams, incoherent to each other, $S_{in,1}$ and $S_{in,2}$. Each beam may be converted to a Jones beam matrix, which will now be described. Normally a light beam is represented by a two-element complex column vector, the Jones vector E.

$$E = \begin{bmatrix} E_x \\ E_y \end{bmatrix} = \begin{bmatrix} E_x e^{i\delta_x} \\ E_y e^{i\delta_x} \end{bmatrix}$$

The Jones vector $E_{in}$ input to a system is transformed to an output Jones vector $E_{out}$ by left multiplication by a two-by-two complex matrix, the Jones matrix J. The Jones matrix can represent any non-depolarizing system.

$$J = \begin{bmatrix} A & B \\ C & D \end{bmatrix}$$

and $$E_{out} = JE_{in}$$

The Jones vector can only represent a fully polarized light beam. Most light beams in nature and in many instruments are only partially polarized and often completely non-polarized. For these the Stokes vector formalism is normally used, sometimes in the equivalent form of coherence matrices. When partially polarized beams are split, converted and recombined (like in some example embodiments disclosed) the Jones formulas above are inadequate. The Stokes vector formalism is also inadequate since it has no way of expressing the absolute phase of two interfering beams. We will therefore describe a method to analyze such instruments.

The equivalence theorem due to Stokes says that the polarization of any beam, also partially polarized, can be represented by the superposition of two partial beams (see 3.1.6.4 in Brosseau). There are many alternative superpositions and the equivalence theorem states that they are equivalent in their polarization-optical properties.

$$S = S' + S''$$

or $$\begin{bmatrix} S_1 \\ S_2 \\ S_3 \\ S_4 \end{bmatrix} = \begin{bmatrix} S_1' \\ S_2' \\ S_3' \\ S_4' \end{bmatrix} + \begin{bmatrix} S_1'' \\ S_2'' \\ S_3'' \\ S_4'' \end{bmatrix}$$

In order for the equivalence theorem to be valid some general assumptions need to be fulfilled, as they are in almost every practical case. One may think of the two partial beams as having a slightly different frequency from each other, thereby over any appreciable measurement time averaging out the instantaneous interference of the electric vector.

There is a special case where any partially polarized beam can be superposed by one non-polarized and one fully polarized beam of light. Another special case is decomposition into fully polarized beams. There are an infinite number of possible decompositions into two fully polarized beams for which the Jones formalism can be used. One special case is a decomposition into two orthogonal polarizations, i.e. beams positioned diametrically opposite on the Poincare sphere and physically having the same ellipticity, perpendicular major axises and opposite sense of rotation of the electric field vector. In general the beams will be of unequal intensity. If they have equal intensity the superposition is non-polarized and if ether of them has zero intensity the superposition is fully polarized.

A general beam with stokes vector S can be decomposed into two fully and orthogonally polarized beams as follows:

$$S = \begin{bmatrix} S_0 \\ S_1 \\ S_2 \\ S_3 \end{bmatrix} = \frac{1+P}{2P} \begin{bmatrix} PS_0 \\ S_1 \\ S_2 \\ S_3 \end{bmatrix} + \frac{1-P}{2P} \begin{bmatrix} PS_0 \\ -S_1 \\ -S_2 \\ -S_3 \end{bmatrix}$$

where P is the degree of polarization:

$$P = \frac{\sqrt{S_1^2 + S_2^2 + S_3^2}}{S_0}$$

The fully polarized partial beams are represented by Jones vectors E' and E" and made to interact with the Jones matrices of the components of the system. If they are recombined later the Jones vectors are added and interference is created. The conversion from a fully polarized Stokes vector to a Jones vector is given in Hauge et al., Appendix A:

$$E = \begin{bmatrix} E_{x0}e^{i\delta_x} \\ E_{y0}e^{i\delta_x} \end{bmatrix} = \frac{e^{i\delta_x}}{2E_{x0}} \begin{bmatrix} S_0 + S_1 \\ S_2 + iS_3 \end{bmatrix}$$

Finally the output Jones vectors can be individually converted to Stokes vectors and added incoherently, i.e. the Stokes vectors are added. In this way, the action by an interferometer on a partially polarized beam can be found.

Since the two states propagate through the same optics it is convenient to collect the two Jones vectors in a 2-by-1 row vector, which when expanded is a two-by-two complex matrix. We have chosen to call it a Jones beam matrix EE:

$$EE = [E' \quad E''] = \left[ \begin{bmatrix} E'_x \\ E'_y \end{bmatrix} \begin{bmatrix} E''_x \\ E''_y \end{bmatrix} \right] = \begin{bmatrix} E'_x E''_x \\ E'_y E''_y \end{bmatrix}$$

The propagation follows the same formula as that for a Jones vector but the input and output are Jones beam matrices:

$$EE_{out} = JEE_{in}$$

The Jones beam matrix carries with it the absolute phase of each partial beam and interfering between beams is possible to analyze. The resulting Jones beam matrix can be reconverted to a Stokes vector which may be partially polarized:

$$S = \begin{bmatrix} |E'_x|^2 + |E'_y|^2 + |E''_x|^2 + |E''_y|^2 \\ |E'_x|^2 - |E'_y|^2 + |E''_x|^2 - |E''_y|^2 \\ \frac{1}{2}(|E'_x + E'_y|^2 - |E'_x - E'_y|^2 + |E''_x + E''_y|^2 - |E''_x - E''_y|^2) \\ \frac{1}{2}(|E'_x + iE'_y|^2 - |E'_x - iE'_y|^2 + |E''_x + iE''_y|^2 - |E''_x - iE''_y|^2) \end{bmatrix}$$

The model above makes it possible to model an interferometer using partially polarized light and to connect any internal state to an output Stokes vector. The output Stokes vector can be measured with a Stokes polarimeter measuring 4 degrees of freedom, i.e. the four Stokes parameters for each elementary measurement. In an example embodiment, a model of an assumed surface is used to calculate the output Stokes vector. If the measured Stokes vector is different from the calculated one, the assumptions about the surface are changed in order to get a better match. When the non-linear fitting of the model of the surface has produced a calculated Stokes vector that matches the measured Stokes vector, the assumed surface parameters are recorded and used as a measurement of the surface parameters. The procedure can be performed in a uniform beam or in a pixel by pixel fashion in an image of the surface.

Measuring the Local Jones Matrix

A fully polarized reflected beam from the surface has four free parameters, namely phase and magnitude in two perpendicular directions, e.g. x and y. However, the surface is generally represented by a Jones matrix with four complex elements. Therefore a single measurement cannot determine all properties of the surface. In order to characterize the surface more fully several measurements with different input polarizations need to be done. One explicit procedure proposed by Clark Jones in 1948 (see Brosseau) uses several incident beams and the determination of the polarization ellipsa for each one of them.

A modern way to do the same would be to make a model of the instrument as described above and measure the reflected state of polarization for a number of input states, then do a non-linear optimization of the matching between the modeled reflected light to the set of measurements by adjusting the elements of the Jones matrix of the surface. The explicit procedure is computationally faster, but the non-linear optimization allows much more freedom in instrumentation. In particular it is more suitable to the described method which extracts more free parameters per measurement and therefore has the capability of determining the Jones matrix of the surface with a smaller set of incident states.

Classical ellipsometry literature deals with a uniform beam measuring the properties of a uniform area on the sample. This is also true for scatterometry where the sample area is patterned, but the pattern is not resolved. One focus of this disclosure is to use polarimetric methods to extract a fuller image of a surface, thereby improving the power of discrimination and making inverse scattering methods more powerful in extracting the physical properties of the surface and structures on it. The determination of the Jones matrix may therefore be done in a point-to-point fashion giving an image with essentially eight free parameters in every point. Other example embodiments may fit the physical sample properties, global, point-by-point, or feature-by-feature, directly to the measurement data without going through a Jones matrix. Other example embodiments may represent the surface properties by local or global Mueller matrices or maps of film thickness, material composition, topography, or of feature size, shape or orientation, and the like.

Modeling the Sample

The electromagnetic modeling of the surface can be done in two ways. Either a local Jones matrix (or Mueller matrix, etc.) is calculated and stored as a local property or the experiment is modeled and the measured value is predicted. The former is more computation intensive, but gives more information about the surface. In one embodiment, it is done by modeling a series of experiments, i.e. calculating the reflected light amplitudes for a number of incident light amplitudes. After the Jones matrix has been calculated, the reflection of any incident light beam can quickly be computed. In the second method, which is suitable for scatterometry and other inverse methods for surface studies, one or several physical experiment are performed and the measurements recorded. Then the same set of experiments is simulated using an electromagnetic model of the surface and the simulated measurement results are compared to the real ones. The physical model is tweaked until the measured and simulated amplitudes agree. This involves either tedious recalculations or the generation of a library of cases, also tedious. In this case, the full Jones matrix may not be needed and time is saved by computing only what is needed.

FIG. 16 shows a procedure for inverse determination of surface parameters The polarimeter may be a polarimetric camera giving a pixel map with Scatterometry This technology can be used for scatterometry. Scatterometry may be defined as recovering properties of features on a sample that do not show clearly in a normal image by analyzing the scattered light. Scatterometry is an application of inverse scattering methods for surface study. Typically the scattered wavefield from a patch of periodic features is collected as a function of angle, polarization, or most commonly wavelength. This technology has enabling characteristics for recovery of surface properties, since the electromagnetic amplitude is recorded for both x and y polarizations (or any other two polarizations). By using the electric field amplitude instead of intensity this technology converges faster to a solution and with fewer false solutions possible.

Furthermore, the technology makes scatterometric analysis of single features possible. The electric field is recorded, but since the detector is an imaging polarimeter the electric field at the detector is an image of the electric field just above the surface of the sample. The electric field is recorded at the same instance with two polarizations with phase and amplitude. The electric field vector is fully known just above the object and can be unambiguously Fourier transformed to the far field, e.g. by FFT. Scatterometers typically work in the far field from a patch of repeating features. However, since the electric field distributions in both the object and the far field are fully known, one may numerically measure the window to certain Fourier components and/or a certain area in the object plane. Only this area need to be used when comparing to the computed scattering pattern and a single feature may be studied with the same precision as a repeating array in a scatterometer in prior art.

Inverse Image Reconstruction

It is known in the art to reconstruct images by combining the measured data, typically an intensity image, and a priori knowledge. See for example U.S. Pat. No. 6,993,204, which is incorporated by reference, where a synthetic image is built from "pixons", elementary image elements, in order to maximize the likelihood to produce the measured or recorded image. The elementary image elements can be chosen according to a priori knowledge about the pattern. If, for example, a microchip contains edges only along the x and y axises, cigar-shaped elements aligned with x and y can be chosen. Inverse image reconstruction may be used to enhance sharpness, reduce noise and to spot minute errors in images such as for defect inspection. This technology produces amplitude images that are less non-linear than prior art images and will therefore support more powerful image enhancement and reconstruction.

Synthetic Aperture Imaging

When a lens is used to form an image it picks up scattered light from a certain range of angles and forms the image with them. The spatial frequencies that pass the lens are limited by the range of angles, i.e. by the NA of the lens. It is not possible to add two pictures taken with the lens moved to pick up different angle ranges and merge the angles into one larger range. The non-linearity of the square-law (intensity) detector in prior art causes strong interaction between different angles and forms a strong background exposure. Otherwise stated, the absence of negative areas in the intensity image makes it impossible to merge the angular ranges of two images. This technology does not have the same limitation. Like with synthetic aperture radar several measurements (images) may be merged into one with higher resolution. The reason is that the electric field amplitude is recorded and may be added merged into one image with an equivalent NA that is the merged angular range. FIG. 17 shows conceptually the merging of two images into one with higher resolution.

CD Metrology

Modern microlithography is extremely sensitive to variations in the width of lines, the distance between lines, the size of islands and holes, and the shape of corners and line ends. Collectively this can be called CD control (Critical Dimension control). It is known that when a feature is smaller than the wavelength (or even smaller than half the wavelength) of the analyzing light, the image produced is not clear and it is difficult to measure the feature's shape or the size in the image. Instead, the size and shape are encoded in the contrast of the line (i.e. the intensity) and the polarization of the reflected light. If it was measured, the absolute phase would also give clues to the linewidth. Other properties of the line, e.g. edge slope or edge roughness, also encode the intensity and polarization. The more parameters that are measured simultaneously, the better discrimination between primary and secondary properties of the line, and the better precision in the interpretation of the data. In an example embodiment, the phase and amplitude of two polarization states are measured for every point in an image of the line. A computer model fits the measured data to a physical model of the line. The linewidth, height, edge slope, and/or line end shortening which fit the data are used as measurements of the same parameters.

Defect Inspection

Defect inspection of wafers, masks, panels for display devices, and similar samples need high throughput and high discrimination against false detections. The more parameters that are measured per pixel on the surface the better discrimination and also the better sensitivity can be achieved. The detection of phase allows high sensitivity for defects that extend in the z direction, e.g. protrusions in large-area production. Using several polarizations allows more discrimination and better classification, as well as more sensitivity to certain shape errors such as non-symmetrical corners. Multiple simultaneous parameters also allow suppression of noise. Noise in a single detector in the polarimeter will have a non-physical character, since the physical changes are mapped as combinations of different detector signals.

Particular Embodiments

One embodiment is a method of collecting optical properties of a test sample in an image plane. This method may include splitting a beam into a reference beam and an illuminating beam, exposing a test sample to the illuminating beam, recombining the reference beam and illuminating beam, detecting image data with one or more image sensors, and extracting from the image data a point-to-point map of polarization, phase and power.

In one aspect of this method, the beam that is split is not fully polarized. In another aspect, the image is detected with an amplitude image detector detecting phase and amplitude of two polarization states. A camera may be used to detect three or four optical parameters for at least one image pixel. The data detected may comprise a Stokes vector for at least one image pixel.

In a further aspect of this method, the detector is an oversampled camera and the electric amplitude is computed from detected pixel-to-pixel variations on the camera.

In some implementations, at least two polarimetric images are recorded for the same sample and where the illumination polarization of the sample changes between the images. The measured data may be used for super resolution processing of the image, or for merging at least two images into one image with higher resolution. Alternatively or in combination, the measured data may be used for measurement of a geometrical property of at least one feature on the sample. The geometric property may be determination of the size of a feature on the sample or determination of the shape of a feature on the sample.

Another aspect of this method is that the recorded image may be stored digitally and where the focal position is changed numerically.

The measured data may be used for defect inspection or classification.

Redundancy among the measured parameters is used for noise suppression.

The method further may include inducing differing polarization states on the reference beam and the illuminating beam prior to recombining the beams.

According to an aspect of this method, the differing polarization states may encode a phase difference between the beams as a result of the recombined beam.

Applying this method may further include splitting the recombined beam into at least first and second split beams and inducing differing polarization states on the split beams.

The method may further include independent, simultaneous determination of phase and power of the polarization states of split beams.

The method may further include varying the reference beam a plurality of times and carrying out the simultaneous determination for the varied reference beams.

Applying the method may further include producing at least four split beams, and also include independent, simultaneous determination of phase and power of the polarization states of the split beams.

Another method embodiment aims to compute the electromagnetic reflecting properties for partially coherent light from a surface. This method includes representing the partially coherent beam by a superposition of at least two fully polarized beams, computing the reflected beam for each of said fully polarized beams, and adding the at least two beams incoherently. This method embodiment may be combined with most or all of the aspects of the preceding method embodiment.

One device embodiment is an aperture for recording an image of a surface with phase and amplitude for two polarization states. This device includes a light source, a beam splitter, an interferometer with a reference and a measure beam, a beam combiner, and a polarimetric camera.

In this device, the light of at least one of the test and measure beams may not be fully polarized.

I claim:

1. A method for optical determination of physical properties of features on a test sample, including:
   splitting a beam that is not fully polarized into a reference beam and an illuminating beam;
   exposing a test sample to the illuminating beam;
   recombining the reference beam and illuminating beam and forming at least one image of the test sample;
   detecting image data from the image of the test sample with at least one image sensor;
   extracting from the image data a point-to-point map of polarization induced by the sample, phase and power; and
   determining from the point-to-point data feature-by-feature physical properties.

2. The method of claim 1, wherein the image is detected with the image sensor that includes a camera detecting at least three optical parameters for at least one image pixel.

3. The method of claim 2, wherein the image sensor detects four optical parameters for at least one image pixel.

4. The method of claim 2, further including suppressing noise using redundancy among the detected optical parameters.

5. The method of claim 1, wherein the image sensor detects data comprising a Stokes vector for at least one image pixel.

6. The method of claim 1, wherein the image sensor is at least one oversampled camera and the electric amplitude is computed from detected pixel-to-pixel variations on the camera.

7. The method of claim 1, further including super resolution processing of the extracted data to enhance the image of the test sample.

8. The method of claim 1, further including merging at least two images into one image with higher resolution.

9. The method of claim 1, further including measuring a geometrical property of at least one feature on the test sample.

10. The method of claim 1, further including determining a size of a feature on the sample.

11. The method of claim 1, further including determining a shape of a feature on the sample.

12. The method of claim 1, further including storing the recorded image digitally and changing a focal position numerically.

13. The method of claim 1, further including performing defect inspection using the extracted data.

14. The method of claim 13, further including performing defect classification using the extracted data.

15. The method of claim 1 further including splitting the recombined beam into at least first and second split beams and inducing differing polarization states on the split beams.

16. The method of claim 15, further including independently and simultaneously determining phase and power of the polarization states of split beams.

17. The method of claim 16, further including varying the reference beam a plurality of times.

18. The method of claim 17, wherein at least four split beams are produced further including independent, simultaneous determination of phase and power of the polarization states of split beams.

19. An optical microscope for characterization of a test sample, including:
   a light source and a beam splitter that splits unpolarized or partially polarized light projected from the light source into an illuminating beam and a reference beam;
   optics that expose the test sample to the illuminating beam;
   a beam recombiner that merges the reference beam and the illuminating beam;
   projection optics that form at least one image of the test sample from the merged beams; and
   at least one imaging polarimeter that records at least one polarization image including point-to-point polarization induced by the sample, and phase and power of the image of the test sample.

20. An optical microscope as in claim 19, wherein said polarization image has pixels and the pixels have a Jones vector with an absolute phase.

21. An optical microscope as in claim 19, wherein said polarization image has pixels and the pixels have a Jones matrix with an absolute phase.

22. An optical microscope as in claim 19, wherein said polarization image has pixels and the pixels have a Stokes vector and an absolute phase.

23. An optical microscope as in claim 19, wherein said polarization image has pixels and the pixels have a Mueller matrix and an absolute phase.

24. An optical microscope as in claim 19, wherein said polarization image has pixels and the pixels have a coherency matrix and an absolute phase.

25. An optical microscope as in claim 19, wherein said imaging polarimeter records components of the polarization sequentially.

26. An optical microscope as in claim 19, wherein said imaging polarimeter records components of the polarization in parallel and simultaneously.

27. A method for optical determination of physical properties of features on a test sample, including:
    splitting a beam into a reference beam and an illuminating beam with a first set of reference and illumination beam polarization states;
    exposing a test sample to the illuminating beam;
    recombining the reference beam and illuminating beam and forming at least one first image of the test sample using the first set of polarization states;
    repeating the splitting, exposing and recombining with a second set of polarization states different from the first set and forming at least one second image of the test sample using the second set of polarization states;
    extracting from image data of the first and second images a point-to-point map of polarization induced by the sample, phase and power; and
    determining from the point-to-point data feature-by-feature physical properties.

28. The method of claim 27, further including determining a size of a feature on the sample.

29. The method of claim 27, further including determining a shape of a feature on the sample.

30. The method of claim 27, wherein at least two polarimetric images are recorded for the same sample and the polarization of the illuminating beam used to expose the test sample changes between the images.

31. The method of claim 1, further including inducing differing polarization states on the reference beam and the illuminating beam prior to recombining the beams.

32. The method of claim 31, whereby the differing polarization states encode a phase difference between the beams in of the recombined beam.

* * * * *

UNITED STATES PATENT AND TRADEMARK OFFICE
CERTIFICATE OF CORRECTION

PATENT NO. : 7,808,648 B2
APPLICATION NO. : 11/742414
DATED : October 5, 2010
INVENTOR(S) : Torbjorn Sandstrom It is certified that error appears in the above-identified patent and that said Letters Patent is hereby corrected as shown below:

In Claim 31, column 18, line 15, delete "1" and insert --27--.

Signed and Sealed this

Seventh Day of December, 2010

David J. Kappos
*Director of the United States Patent and Trademark Office*